(12) United States Patent
Shin (10) Patent No.: US 11,613,730 B2
(45) Date of Patent: Mar. 28, 2023

(54) METHOD OF CULTURING NK CELLS AND KITS CONTAINING MEDIUM ADDITIONS

(71) Applicants: Dong Hyuk Shin, Gyeonggi-do (KR); NKCL BIO GROUP INC., Gyeonggi-do (KR)

(72) Inventor: Dong Hyuk Shin, Seongnam-si (KR)

(73) Assignees: Dong Hyuk Shin, Gyeonggi-Do (KR); NKCL BIO GROUP INC., Gyeonggi-Do (KR)

( * ) Notice: Subject to any disclaimer, the term of this patent is extended or adjusted under 35 U.S.C. 154(b) by 130 days.

(21) Appl. No.: 15/998,432

(22) Filed: Aug. 15, 2018

(65) Prior Publication Data

US 2018/0355317 A1  Dec. 13, 2018

Related U.S. Application Data

(63) Continuation-in-part of application No. PCT/KR2016/015392, filed on Dec. 28, 2016.

(30) Foreign Application Priority Data

Feb. 15, 2016 (KR) .................. 10-2016-0017073

(51) Int. Cl.
| | | |
|---|---|---|
| *C12N 5/0783* | (2010.01) | |
| *C07K 16/28* | (2006.01) | |
| *A61K 35/17* | (2015.01) | |
| *A61P 35/00* | (2006.01) | |

(52) U.S. Cl.
CPC ............ *C12N 5/0646* (2013.01); *A61K 35/17* (2013.01); *C07K 16/2803* (2013.01); *C07K 16/283* (2013.01); *C07K 16/2809* (2013.01); *A61P 35/00* (2018.01); *C12N 2500/38* (2013.01); *C12N 2501/2302* (2013.01); *C12N 2501/2318* (2013.01); *C12N 2501/515* (2013.01); *C12N 2501/599* (2013.01)

(58) Field of Classification Search
CPC .......... C12N 5/0646; C12N 2501/2302; C12N 2501/2318; A61K 35/17; C07K 16/283
See application file for complete search history.

(56) References Cited

U.S. PATENT DOCUMENTS

| | | | | |
|---|---|---|---|---|
| 2013/0157364 A1* | 6/2013 | Hong | ................. | C07K 16/2809 435/375 |
| 2013/0295671 A1* | 11/2013 | Deng | ..................... | A61P 37/04 435/375 |
| 2016/0068811 A1* | 3/2016 | Kokaji | ................. | C12N 5/0636 435/372.3 |

FOREIGN PATENT DOCUMENTS

| | | | |
|---|---|---|---|
| KR | 10-2009-0127973 | A | 12/2009 |
| KR | 10-1039843 | B1 | 6/2011 |
| KR | 10-2013-0033354 | A | 4/2013 |
| KR | 10-101415039 | B1 | 8/2014 |
| KR | 10-2015-0029691 | A | 3/2015 |
| KR | 101683614 | B1 | 12/2016 |

OTHER PUBLICATIONS

English translation of KR20090127973; Lee et al. p. 1-7. (Year: 2009).*
International Search Report for Corresponding Korean Patent Application No. PCT/KR2016/015392 (2 Pages) (dated Apr. 19, 2017).

* cited by examiner

*Primary Examiner* — Taeyoon Kim
(74) *Attorney, Agent, or Firm* — The PL Law Group, PLLC (57) ABSTRACT

The present invention relates to a method for culturing natural killer cells (NK cells) applied to immune therapy and, more particularly, to a medium addition kin for culturing NK cells with which lymphocytes derived from human peripheral blood can be cultured to effectively amplify and activate NK cells, which have an outstanding therapeutic effect on malignant tumors, while remarkably increasing the share of NK cells, and an NK cell culturing method using the kit.

4 Claims, 4 Drawing Sheets

METHOD OF CULTURING NK CELLS AND KITS CONTAINING MEDIUM ADDITIONS

CROSS-REFERENCE TO RELATED APPLICATIONS

This application is a continuation-in-part of PCT/KR2016/015392, filed Dec. 28, 2016, which claims the benefit of Korean Patent Application No. 10-2016-0017073 filed Feb. 15, 2016, the contents of each of which are incorporated herein by reference.

FIELD OF THE INVENTION

The present invention relates to a method for culturing natural killer cells (NK cells) applied to immunotherapy, and more particularly, to a method for culturing NK cells, which is effective for treating malignant tumors, by culturing lymphocytes derived from human peripheral blood Which is capable of efficiently amplifying and activating NK cells and significantly increasing the proportion of NK cells, and a method for culturing NK cells using the kit.

BACKGROUND OF THE INVENTION

Immunotherapy is a method of infusing a patient with strong acting immune cells such as natural killer cells (NK cells), dendritic cells (DC), B cells, T cells, etc. extracted from the patient's blood. Since the blood of the patient is used, the side effect is less than that of conventional chemotherapy and the administration method is simple and has been actively studied recently.

Among the immune cells activated by immunotherapy, NK cells have a characteristic as a large granular lymphocytes (LGLs), that are excellent in killing infected viruses and tumor cells, but do not kill most normal cells. The anticancer mechanism of the NK cells is necrosis, apoptosis, or both. NK cells respond to cytokines such as IL-2, IL-12, and interferon, thereby elevating cytotoxicity, secretory, and proliferative functions. The phenotypes of NK cells in human are CD16 (FcγRIII) and CD56, which are used as markers for NK cells as they do not express TRC (T-cell receptor complex) on the cell surface.

Such NK cells are known to play an important role in early defense mechanisms and tumor immunity of the human body. NK cells kill specific auto-cells, allogeneic cells, and even xenogeneic cancer cells without immunological acquisition due to the expression of Major Histocompatibility Complex (MHC). In particular, NK cells kill target cells better that are less or not expressing Class 1 MHC. Thus, NK cells can effectively kill most cancer cells that do not express MHC, as well as kill some virus-infected cells and bacteria such as *Salmonella typhi*.

As described above NK cells exert an excellent effect on cancer cell. However, only 5% to 15% of peripheral blood lymphocytes are NK cells in normal persons and the percentage decreases to less than 1% in the cancer patients which gives a limitation in effectively attacking cancer cells without a separate amplification step.

Cytokine such as IL-2 and antibodies such as CD3 are used to activate and proliferate immune cells, particularly NK cells. CD3 antibody plays a very important role in the proliferation of immune cells in the current technology. The problem is that it is very difficult to activate immune cells using this antibody. That is, the current common technique in immune cell culture is to immobilize CD3 antibody in a flask and to stimulate it for a predetermined time. However, everyone differs in susceptibility to immune cells and even the cell culture conditions differ in the skill level of the operator. For example, when the stimulation of the CD3 antibody is low or almost not, the immune cells do not proliferate well. In addition, when stimulation is too high, NK cells hardly proliferate on the other hand NKT cells or T cells proliferate. In this case, since T cells are particularly proliferated, it is not easy to obtain a large number of NK cells.

When a strong stimulus of CD3 antibody is applied from the beginning, immature progenitor cells will mature into T cells. Therefore, the current generally used method, stimulating CD3 antibody slightly, is difficult to obtain activated NK cells proliferated in large quantities as they are highly influenced by the individual difference or the surrounding environment.

SUMMARY OF THE INVENTION

A certain embodiment of the present invention provides a stable NK cell culture method in which the ratio of T cells is low, and the ratio of NK cells is remarkably high, by sequentially adding medium additives to the lymphocyte culture medium by specific order to stimulate lymphocytes.

Another embodiment of the present invention provides a culture medium addition kit comprising a composition for stably amplifying NK cells in a final lymphocyte culture solution while eliminating the cumbersome process of culturing lymphocytes (immune cells) for a predetermined time while incubating immobilized anti-CD3 antibodies in a culture container to stimulate lymphocytes.

Still another embodiment of the present invention provides a NK cell culture solution prepared by using the NK cell culture method and the NK cell culture medium addition kit thereof.

DETAILED DESCRIPTION OF THE INVENTION

A certain embodiment of the present invention provides a method for stably amplifying NK cells in a lymphocyte culture solution without removing immobilized CD3 antibody after the stimulation.

One embodiment of the present invention is to provide a stable NK cell culture method in which the ratio of T cells is low, and the ratio of NK cells is remarkably high, by sequentially adding medium additives to the lymphocyte culture medium by specific order to stimulate lymphocytes.

Another embodiment of the present invention provides a culture medium addition kit comprising a composition for stably amplifying NK cells in a final lymphocyte culture solution while eliminating the cumbersome process of culturing lymphocytes (immune cells) for a predetermined time while incubating immobilized anti-CD3 antibodies in a culture container to stimulate lymphocytes.

Still another embodiment of the present invention provides a culture medium addition kit and the culture method thereof capable of culturing NK cells very easily by standardizing the culture medium additives which should be added during the culture step so that NK cells can proliferate in a significantly higher ratio during lymphocyte culture.

Yet another embodiment of the present invention provides a culture medium for culturing NK cells prepared by using the culture method and the culture medium addition kit thereof.

The present invention also provides the culture medium addition kit for culturing NK cells comprising:

a B unit comprising a basic solution comprising IL-2, L-glutamine and a cell culture medium (about 3600 IU/mL of IL-2 and 5 µM/mL of L-glutamine);

a C1 unit comprising a cytokine 1 solution comprising IL-12 and IL-18 dissolved in the basic solution, wherein a concentration of IL-12 is 0.5-5 ng/mL and a concentration of IL-18 is 2-50 ng/mL;

a C2 unit comprising a cytokine 2 solution comprising IL-15 dissolved in the basic solution, wherein a concentration of IL-15 is 10-35 ng/mL;

an A1 unit comprising an antibody 1 solution comprising an anti-CD16 antibody and an anti-CD56 antibody dissolved in the basic solution, wherein concentrations of anti-CD16 antibody and anti-CD56 antibody are 0.1-15 µg/mL;

an A2 unit comprising an antibody 2 solution comprising the antibody 1 solution and the basic solution in a volume ratio of 1:6-10; and a D unit comprising an antibody-cytokine mixed solution comprising an anti-CD3 antibody dissolved in the cytokine 1 solution, wherein a concentration of the anti-CD3 antibody is 1-12 µg/mL.

In a preferred embodiment, the A1 unit is added to the lymphoid culture medium prior to the D unit.

In a preferred embodiment, the anti-CD16, anti-CD56 and the basic solution contained in the A1 Unit are packaged separately, mixed in the medium addition step.

In a preferred embodiment, anti-CD16, anti-CD56 and basic solution of the antibody 1 solution, and basic solution contained in A2 unit are separately packaged and mixed in the medium addition step.

In a preferred embodiment, the anti-CD3 and cytokine 1 solutions contained in the D unit are separately packaged and mixed in the medium addition step.

In a preferred embodiment, the units are configured to be added to the lymphocyte culture medium in the order of A1 unit, D unit, C1 unit, A2 unit, C2 unit, A2 unit and B unit.

The present invention provides a method for culturing NK cell comprising:

a) adding an antibody 1 solution to a separated lymphocyte followed by adding autologous plasma;

b) adding an antibody-cytokine mixed solution to the medium collected from step a);

c) adding a cytokine 1 solution to the medium collected from step b) followed by adding autologous plasma;

d) adding an antibody 2 solution to the medium collected from step c) followed by adding autologous plasma, FBS or the like;

e) adding a cytokine 2 to the medium collected from the step d) followed by adding autologous plasma, FBS or the like;

f) adding an antibody 3 solution and autologous plasma, FBS or the like to the medium collected from step e); and g) adding a basic solution and autologous plasma, FBS or the like to the medium collected from step f).

In a preferred embodiment, the antibody 3 solution uses a portion of the antibody 2 solution.

In a preferred embodiment, the autologous plasma comprises more than 40 usp units of heparin per 1 mL of blood.

In a preferred embodiment, the added amount of autologous plasma, FBS or the like is less than 10% by volume of the total medium.

In a preferred embodiment, the interval between the first step and the second step is 24 hours or more.

In a preferred embodiment, the step d) and the step f) are each cultured in a culture vessel having a larger volume than the previous step.

The present invention also provides an NK cell culture solution cultured by any one of the NK cell culture media cultured by the above-described culturing method or with any one of the above-described media addition kits described above.

In a preferred embodiment, the number of cells contained in the NK cell culture solution is $3.1 \times 10^9$ or more, and the ratio of NK cells is 80% or more.

The present invention has the following advantages.

First, the NK cell culture medium addition kit of the invention provides a method for stably amplifying NK cells from lymphoid culture medium while removing the cumbersome process of culturing cells with immobilized anti-CD3 antibody to stimulate lymphocytes in a predetermined period of time.

In addition, the NK cell culture method of the present invention provides stable and active lymphocytes in which the ratio of T-cells is low, and the ratio of NK cells is remarkably high, by sequentially using additives constituting units included in the medium addition kit by specifying the order in which the lymphocytes are stimulated.

Also, according to the present invention, NK cells can be easily cultured by standardizing culture medium additives which must be added during culturing step so that NK cells can proliferate in a significantly higher ratio during lymphocyte culture.

The terminology used herein is to describe particular embodiment only and is not intended to be limiting of the invention. The expression of the singular forms "a", "an" and "the" include plural representations unless the context clearly dictates otherwise. In the present application, the terms "comprise" or "include" are used to refer to the features, numbers, and structures described in the specification, steps, operations, components, parts, or combinations thereof, are intended to specify the existence of one or more other features or numbers, it is to be understood that the present invention does not preclude the existence or addition of a step, an operation, a component, a part, or a combination thereof.

It will be understood that, although the terms first, second, etc. may be used herein to describe various elements, these elements should not be limited by these terms. The terms are used to distinguish one element from another. For example, the first component can be referred to as a second component without departing from the scope of the present invention, similarly, the second component can be referred to as a first component.

Unless otherwise defined, all terms used herein, including technical or scientific terms, have the same meaning as commonly understood by one of ordinary skill in the art to which this invention belongs. It will be understood that terms, such as those defined in commonly used dictionaries, should be interpreted as having a meaning that is consistent with their meaning in the context of the relevant art, and not to be interpreted in an idealized or overly formal sense unless expressly so defined herein.

Hereinafter, the technical structure of the present invention will be described in detail with reference to the accompanying drawings and preferred embodiments.

However, the present invention is not limited to the embodiments described herein and may be embodied in other forms. Like reference numerals used to describe the present invention throughout the specification represent the same elements.

Kits for Culturing NK Cells

The technical feature of the present invention is the NK cell culture medium addition kit comprising the composition for stably amplifying NK cells in the final lymphocyte culture solution while eliminating the cumbersome process of culturing lymphocytes (immune cells) for the predetermined time while incubating immobilized anti-CD3 antibodies in a culture container to stimulate lymphocytes, and the culture method using the same.

In other words, in the present invention, NK cells can stably proliferate up to 5,000 times or more at a minimum of 500 times by pre-stimulating with anti CD16 and anti CD56 antibody and then adding anti-CD3 antibody in the medium after about 24-48 hours.

In accordance with the experiment result showing that when immature progenitor cells were induced to differentiate into NK cells and pre-matured NK cells were activated with anti-CD16 and anti-CD56 antibodies, followed by NK cells activation by anti-CD3 antibody stimulated T cells, NK cells were proliferated in large quantities until anti-CD3 antibodies was degraded in the culture medium even with the additional stimulus. To stimulate lymphocytes, it is possible to culture lymphocytes in a very high ratio of NK cells without the cumbersome process of culturing the lymphocytes (immune cells) for the predetermined time while incubating immobilized anti-CD3 antibodies in the culture container.

The present invention relates to the medium-added kit for the NK cell culture, which is individually packaged so that it can be added to the medium in each step of the culture, comprising different components such as the B unit, the C1 unit, the C2 unit, the A1 unit, the A2 unit and the D unit. Here, these units are determined to be included in consideration of the influence on the lymphocyte culture medium so that most of the cells cultured in the lymphocyte culture can be NK cells. The NK cells can be stably grown at least 500 to 5000 times as compared with the conventional culture method, in the order of the A1 unit, the D unit, the C1 unit, the A2 unit, the A2 unit and the B unit to the lymphocyte culture medium.

First, the B unit comprises the basic solution, wherein the basic solution comprising IL-2, L-glutamine, and the cell culture medium. The amount of IL-2 is about 100 ng/mL-300 ng/mL, preferably about 200-250 ng/mL (3240 IU/mL to 4000 IU/mL).

IL-2 is a glycoprotein having a molecular weight of 14-17 kDa, which is made when T cell is activated by recognizing an antigen. IL-2 is secreted from the T cells, reacts with T cells produced by, and promotes the growth of T cells. IL-2 also promotes growth and enhances the killing ability of NK cells, and promotes the growth of B cells. L-glutamine is an ingredient which acts as a nutrient for immune cell culture. A cell culture medium can be a basic culture medium for floating cells.

As a specific embodiment of the B unit, 2 mg of IL-2 and 100 ml of a 500 mM L-glutamine solution are added to the basic culture medium for floating cells (a commercially available cell culture medium, if IL-2 or L-glutamine is already present in the basic medium, the amount thereof is adjusted so as to adjust the final concentration) to obtain a final solution of 10 L to prepare the basic solution.

The C1 unit comprises the cytokine 1 solution, wherein the cytokine 1 solution comprises IL-12, IL-18, and the basic solution. Herein, the amount of IL-12 in the cytokine 1 solution is about 0.5 ng/ml-5 µg/ml, preferably 1 ng/mL-3 ng/ml, more preferably 1.5 µg/mL-2.5 µg/mL. The amount of IL-18 in the cytokine 1 solution is about 2 ng/ml-50 ng/ml, and preferably 8-20 ng/mL, and more preferably 11 ng/mL-15 ng/mL.

IL-12 is produced in dendritic cells (DC) and macrophages and B cells. IL-12 induces the production of IFN-γ and TNF-a from NK cells and T-lymphocytes and reduces the production of IL-4 which inhibits IFN-γ. In addition, increases the cytotoxicity of NK cells and CD8+ cytotoxic T-lymphocytes. IL-12 has a close relationship with an IL-2 signal transduction system in NK cells. Also, IL-2 induces the expression of IL-12 β1 receptor and IL-12 β2 receptor in NK cells, thereby expressing and activating proteins related to IL-12 signal transduction system. This mechanism is well noted in IFN-γ production capability and the target cell killing ability of NK cells. IL-12 β2 receptor appears to play an important role in IL-12 function, the studies have been reported that it suppresses the production of Th2 and stimulates the production of Th1. IL-12 signaling in T cells and NK cells is involved in the JAK-STAT signaling pathway and the activity of IL-12 β2 receptor plays an important role in inducing and activating the phosphorylation of the transcription factor STAT4.

IL-18 is a proinflammatory cytokine gene which is also produced from macrophages. IL-18 binds to the IL-18 receptor and, in conjunction with IL-12, causes an immune response to bacteria or virus-infected cells and increases IFN-γ production in NK cells and T cells.

As a specific example of the C1 unit, 10 µg of IL-12 and 50 µg of IL-18 were dissolved in water to make 10 ml of cytokine solution (the IL-12 concentration: 1 µg/mL and the IL-18 concentration: 5 µg/mL). The cytokine 1 solution is prepared by dissolving 1 mL of above cytokine solution in 500 mL of basic solution, so that IL-12 is contained at a concentration of 2 ng/mL and IL-18 is contained at a concentration of 10 ng/mL.

The C2 unit comprises the cytokine 2 solution, wherein the cytokine 2 solution comprises IL-15 and the basic solution. The concentration of IL-15 in the cytokine 2 solution can be 10 ng/mL-50 ng/mL, preferably 15 ng/mL-25 ng/mL.

As is well known, IL-15 is a pleiotropic cytokine which belongs to the four-helix bundle cytokine family and is known to play an important role in proliferation, survival and differentiation. In addition, IL-15 is expressed in a wider variety of cells, and thus can be more broadly regulated than IL-2. It affects each phase of the immune response and acts on many types of cells involved in the immune response at each stage. A series of studies have shown that IL-15 is directly involved in the formation of memory T cells.

As a specific embodiment of the C2 unit, the cytokine 2 solution can be prepared by dissolving IL-15 in the basic solution to a concentration of 20 ng/mL.

The A1 unit comprising the antibody 1 solution, wherein the antibody 1 solution comprises anti-CD16, anti-CD56 and the basic solution. The concentration of anti-CD16 and anti-CD56 in the antibody 1 solution can be 0.1-2.0 µg/mL, preferably 0.5-0.7 µg/mL, respectively.

As is well known, CD16 and CD56 are surface proteins of NK cells. When a lymphocyte is cultured in the presence of the anti-CD16 antibody or an antigen-antibody complex, CD16 antigen is added to NK cells to cause signal transduction. Transferrin receptors such as the α-chain of the IL-2 receptor can be expressed, or tumor necrosis factor (TNF) or IFN-γ can be produced from NK cells. The anti-CD56 antibody also performs a similar function to the anti-CD16 antibody.

As a specific example of the A1 unit, 6 µL of the each anti-CD16 and anti-CD56 solutions (1 mg/mL) are dissolved in 10 mL of the basic solution to prepare the antibody 1 solution.

The A2 unit comprises the antibody 2 solution, wherein the antibody 2 solution comprising the antibody solution 1: basic solution in a volume ratio of 1:6 to 10. In a specific embodiment of the A2 unit, the antibody solution 2 can be prepared by mixing 30 ml of the basic solution in 6.5 ml of the antibody 1 solution. Some of the antibody 2 solution may constitute the A2 unit, and some may constitute the A3 unit.

The A1 unit to the A3 unit can be used for 1 to 2 months in the refrigeration storage when the antibody is already added to the basic solution. In order to increase the shelf life, the anti-CD16, anti-CD56, and the basic solutions are separately packaged and mixed during the medium addition step to form antibody 1 solution, antibody 2 solution and antibody 3 solution, respectively.

The D unit comprises the antibody-cytokine mixed solution, wherein the antibody-cytokine mixed solution comprising the anti-CD3 and the cytokine 1 solution. In this case, the content of the anti-CD3 is 1 µg/mL-12 µg/mL, preferably 3 µg/mL-8 µg/mL, more preferably 4 µg/mL-5 µg/mL.

T cells are activated upon receipt of a signal through the TCR, but the TCR α or β chain cannot carry the activation signal by itself and transmit the signal through the CD3 chain around the TCR. In other words, when the TCR recognizes an antigen, the CD3 antigen transmits the signal into the cell. For example, when the TRC binds to the MHC+antigen, the TCR binds to the CD3 antigen (γ, δ, ε, ζ or η) and the CD3 antigen gives a signal into the cell.

As a specific example of the D unit, the antibody-cytokine mixed solution can be prepared by dissolving 5 µL of the anti-CD3 solution (1 mg/mL) in 1 mL of the cytokine 1 solution.

The D unit can be used for 1 to 2 months in the refrigeration storage when the antibody is already added to the cytokine 1 solution. Therefore, to extend shelf life the anti-CD3 and the cytokine 1 solution constituting the D unit can be packaged separately and mixed during the medium addition step to form the antibody-cytokine mixed solution. In this case, the shelf life can be extended for more than six months.

Method for Culturing NK Cells

The present invention provides the NK cell culture method comprising:

a) adding an antibody 1 solution to a separated lymphocyte followed by adding autologous plasma;

b) adding an antibody-cytokine mixed solution to the medium collected from step a);

c) adding a cytokine 1 solution to the medium collected from step b) followed by adding autologous plasma;

d) adding an antibody 2 solution to the medium collected from step c) followed by adding autologous plasma, FBS or the like;

e) adding a cytokine 2 to the medium collected from the step d) followed by adding autologous plasma, FBS or the like;

f) adding an antibody 3 solution and autologous plasma, FBS or the like to the medium collected from step e); and g) adding a base solution and autologous plasma, FBS or the like to the medium collected from step f).

The method can also utilize the above-described culture medium addition kit for NK cell culture.

Here, the antibody 3 solution uses a portion of the antibody 2 solution. The added amount of autologous plasma, FBS or the like is less than 10% by volume of the total medium. The step d) and the step f) are each cultured in a culture vessel having a larger volume than the previous steps.

The autologous plasma added during the culturing step of the present invention contains at least three times or more heparin than the amount contained in the known culture method. In other words, blood does not coagulate during blood collection when heparin is used at a concentration of 158 usp unit per 10 mL of blood, but coagulation occurs, when heparin is added to the cell culture medium at a concentration of 158 usp unit per 5 ml of plasma, which inhibits the cell growth. However, in the present invention, it was confirmed that cells can be cultured well without coagulation even if at least three times more heparin concentration is used than the usual amount, so there is no problem in culturing even when using 3 to 4 times or more of heparin than known respectively. In addition, the proteins such as complement as well as the active ingredients for cell culture are removed by heating at 56° C. for 30 minutes in the general plasma inactivation method. However, the present invention when using 3 times or more of heparin concentration without using the plasma inactivation method, only a small amount of plasma can be used as there is no loss of active ingredients for the culture. For example, the conventional method uses 10% or more of plasma by volume of the culture solution, but in the present invention, it was confirmed that the cultivation can be performed less than 10% of plasma, even 3% to 7% of plasma by volume was sufficient. Thus, the autologous plasma used in the culture method of the present invention may contain 40 usp unit or more, preferably 50-60 usp unit or more of heparin per 1 ml of blood.

In addition, at least 24 hours of interval is need between the step a) and step b), to sufficiently stimulate lymphocytes with the anti-CD16 and anti-CD56 of the antibody 1 solution in the presence of IL-2. When step b) is performed, the anti-CD3 antibody contained in the D solution is added to the medium without being immobilized. NK cells proliferate without problem until the anti-CD3 antibody is degraded in the culture medium respectively, even further stimulation has occurred.

It is well known that the conventional immune cell is cultured for 14 days to 17 days, at which time the most proliferated immune cells can be obtained. In the present invention, cells are transferred into a 1 L bag after 14 to 17 days of culture, no additional cytokine or antibody is added to stimulate the immune cells. That is, since the immune cells have already been sufficiently stimulated, they continue to proliferate in the 1 L bag. After the immune cells are sufficiently proliferated, apoptosis occurs as there is a proliferation limit. Therefore, it is possible to expect an anticancer effect by maximally increasing the number of immune cells over about 14 days. However, it is also possible to consider the method of harvesting the antibody before transferring to the 1 L bag. In this case, the number of immune cells ($5\times10^7$-$25\times10^7$) administered to the patient is smaller than that of 14 days, but it is possible to live longer and to proliferate until reaching the limit as there are many young immune cells that have not reached the growth limit yet and expect a different effect compare to the previous method. The anticancer effect or the cancer prevention effect may vary depending on the type of cancer, the period of time, or the characteristics of the immune system of a person, so that it may be preferable to cultivate 14 days for some people and preferable to cultivate about 7 to 8 days in a flask.

EXAMPLE

Selected embodiments of the invention are described in further details with reference to the following examples. These examples are for illustrative purposes only and are not intended to limit the scope of the invention.

Example 1

The NK cell culture medium addition kit was prepared as follows:

1. The preparation of the B unit 2.2 mg of IL-2 and 100 mL of 500 mM L-glutamine solution were added to the basic culture medium for floating cell (if the amount of IL-2 or L-glutamine already exists in the basic medium, the amount is adjusted to adjust the final concentration) to prepare the basic solution (B solution). The B unit was prepared using 3.8 L of this solution: 36 mL of the B solution was placed in each container, labeled as "B solution, day 7" and stored in the refrigerator. The remaining 6.2 L was used to prepare other units.

2. The Preparation of the C1 unit

20 µg of IL-12 and 125 µg of IL-18 were dissolved in distilled water to make 10 mL cytokine solution (C solution). The C solution (1 mL) was added in 500 mL of the basic solution (B solution) to prepare the cytokine 1 solution (C1 solution). The C1 unit was prepared using the 390 mL of this C1 solution: 4.5 mL of the solution was placed in each container, labeled as "C1 solution, day 3" and stored in the refrigerator. The remaining was used to prepare the D unit.

3. The Preparation of the C2 unit

20 µg of IL-15 was dissolved in the B solution to make 1000 ml cytokine 2 solution (C2 solution). The C2 unit was prepared by 9 mL of the C2 solution was placed in each container, labeled as "C2 solution, day 5" and stored in the refrigerator.

4. The Preparation of the A1 unit

Antibody 1 solution (A1 solution) was prepared by dissolving 0.5 mg of each of anti-CD16 and anti-CD56 antibodies in 830 mL of the B solution. The A1 unit was prepared by 3.5 mL of the antibody 1 solution was placed in each container, labeled as "A1 solution, day 0", and store in the refrigerator. The remaining solution was used to prepare A2 and A3 units.

5. The Preparation of the A2 and the A3 units 530 mL of the A1 solution and 3000 mL of the B solution were mixed to prepare the antibody 2 solution (A2 solution). The A2 unit was prepared by 9 mL of the A2 solution was placed in a container, labeled as "A2 solution, day 4" and store in the refrigerator. The A3 unit was prepared by 27 ml of the A2 solution placed to another container, labeled as "A3 solution, day 6", and stored in the refrigerator. As the A1 solution and the A2 solution have a short shelf life of one month or less, they can be prepared as follow.

Each 6 µL of anti-CD16 (1 mg/mL) and anti-CD56 (1 mg/mL) antibody solution and 10 mL and 30 mL of the B solution were packed separately to prepare A1 to A3 units and can prepare A1 to A3 solution by mixing all of them in use. First, the A1 unit is prepared by 6 µL of the anti-CD16 and anti-CD56 antibodies were dissolved in 10 mL of the B solution, 3.5 mL of A1 solution was placed in to a container, labeled as "A1 solution, day 0" and stored in the refrigerator. About 6.5 mL of the remaining A1 solution was mixed with 30 mL of the B solution to prepare A2 solution. 9 mL of the prepared A2 solution was labeled as "A2 solution, day 4" and stored in the refrigerator to prepare the A2 unit. The remaining 37 mL was labeled "A3 solution, day 6" to prepare the A3 unit and store it in the refrigerator. In this case, their shelf-life may be extended to more than six months.

6. The Preparation of the D unit

The antibody-cytokine mixed solution (D solution) was prepared by dissolving 500 µg of the anti-CD3 antibody to the C1 solution to make 105 mL. The D unit was prepared by 1 mL of the D solution was placed to a container, labeled as "D solution, day 1" and stored in the refrigerator. As the solution D has a short shelf life of one month or less, it can be prepared as follows.

5 µL of the anti-CD3 antibody solution (1 mg/mL) and 1 mL of the C1 solution were packed in separate containers to prepare the D solution, and the D unit can be prepared by mixing them at the time of use. In other words, the D unit was prepared before use by dissolving 5 µL of anti-CD3 antibody in 1 mL of C1 solution, labeled as "D1 solution, day 1", and stored in the refrigerator. In this case, the shelf life may be extended to six months or more.

7. The Preparation of the kit for NK cell culture medium

The NK cell culture medium addition kit can be prepared by arranging medium of the B unit, the C1 unit, the C2 unit, the A1 unit, the A2 unit (which can be separated into the A2 unit and the A3 unit, if necessary) and the D unit. If necessary, the order of the medium can be arranged in the order of the A1 unit, the D unit, the C1 unit, the A2 unit, the C2 unit, the A2 unit (the A3 unit) and the B unit.

Example 2

After preparing lymphocytes and autologous plasma from the blood from the patient, NK cells were cultured using the culture medium addition kit for NK cell culture obtained in Example 1 as follows:

1. Lymphocyte extraction and autologous plasma preparation

The blood of a patient to be treated is superimposed on a Ficoll-Paque Plus solution having a specific gravity of 1.077 and centrifuged at a constant centrifugal force. As human lymphocytes or mononuclear cells have the specific gravity lower than 1.077, the red blood cells and granulocyte layers having the specific gravity larger than 1.077 were down, and the mononuclear cell layer and the platelets having the specific gravity smaller than 1.077 were separated to obtain a mononuclear cell layer containing the lymphocytes, and only the lymphocytes were extracted from the separated mononuclear cell layer.

More specifically, 30 ml of the peripheral blood of patient A was placed in a 50 ml conical tube, centrifuged, and the upper plasma of the autologous plasma was placed in a heparin tube and then placed in a new 50 ml conical tube and centrifuged again. Segments were prepared as autologous plasma.

After that, PBS was added to the blood tube from which plasma was removed, and the volume was adjusted to 30 ml. Then, the mixture was transferred to a tube containing Ficoll-Paque Plus and centrifuged at 800×g for 15 minutes. The buffy coat layer was separated and collected in a 50 ml conical tube, adjusted to a volume of 50 ml with PBS, and then mixed. Then, the supernatant was discarded by centrifugation 2-3 times and the lymphocytes were separated. The number of lymphocyte cells obtained at this time was $1.0$-$2.0 \times 10^7$.

2. The first step of adding the antibody 1 solution of the A1 unit to the isolated lymphocytes followed by adding the autologous plasma as follows.

Prepared lymphocytes were dissolved in a vial (3.5 mL) of the A1 solution (day 0), placed in T25 flask, added 0.25-0.5 mL of prepared autologous plasma and incubated in an incubator.

3. The second step of adding the antibody-cytokine mixed solution of D unit to the medium from the first step as follows.

After observing the cells with a microscope, 1 vial (1 mL) of the D solution (day 1) was added to the T25 flask with a gentle shake and incubated in the incubator.

4. The third step of adding the C1 unit cytokine 1 solution to the medium from the second step followed by adding the autologous plasma as follows.

After observing the cell status, 1 vial (4.5 mL) of the C1 solution (day 3) was added and adding 0.25 mL-0.5 mL of autologous plasma was followed and continued culturing in the incubator.

5. The fourth step of adding the A2 solution of antibody 2 to the medium from the third step followed by adding autologous plasma or FBS as follows.

Scraped the bottom of the incubated T25 flask with a scraper and transferred all the cells to a T75 flask. Added 1 vial (9 mL) of the A2 solution (day 4) and 0.5 mL-1 mL of autologous plasma or FBS (or similar) with a gentle shake and continued culturing in the incubator.

6. The fifth step of adding the C2 solution of cytokine 2 solution to the medium from the fourth step followed by adding autologous plasma or FBS as follows.

1 vial (9 mL) of C2 solution (day 5) and 0.5 mL-1 mL of autologous plasma or FBS (or similar) were added to the incubated T75 flask with a gentle shake and continued culturing in the incubator.

7. The sixth step of adding antibody 3 solution and autologous plasma or FBS to the medium from the fifth step as follows.

Scraped the bottom of the incubated T75 flask with a scraper and transferred all the cells to the T150 flask. Added 1 vial (27 mL) of the A3 solution (day 4) and 1.5 mL to 3 mL of autologous plasma or FBS (or similar) with a gentle shake and continued culturing in the incubator.

8. The seventh step of adding the basic solution of the B unit and the autologous plasma or FBS to the medium from the sixth step as follows.

1 vial (36 mL) of the B solution (day 7) and 2 mL-4 mL of autologous plasma or FBS (or the like) were added to the incubated T150 flask, with a gentle shake and continued culturing in the incubator.

9. Cell harvesting step after the mass culture

The bottom of the cultured T150 flask was scraped off. After confirming the cells, 10 ml of all the remaining plasma or FBS (or similar) in the cells and the culture medium was added to make a cell suspension. After the cell suspension was added to the 1 L of $CO_2$ permeability culture bag, the cells were massaged as to mix well with the culture medium, and then the cells were spread evenly in a 37° C., 5% $CO_2$ incubator, incubated for 4 to 5 days. After the incubation, the final culture is placed in a centrifuge tube, and the cells are harvested by centrifugation several times. The harvested cells can be stored in a saline bag, refrigerated or frozen. The final number of cells obtained by culturing the lymphocytes isolated from 30 mL of patient A blood was $3.14 \times 10^9$.

In some cases, the cells can be immediately harvested without the mass culture at this stage. The number of immune cells obtained after 8 days of culture was $12.7 \times 10^7$ cells.

Example 3

The same procedure as in Example 2 was carried out except that the blood used was not the patient A but blood of the patient B. The number of immune cells obtained after 8 days of culture was $17.5 \times 10^7$ and the final lymphocytes isolated from the blood of patient B was $4.33 \times 10^9$ cells.

Example 4

The same procedure as in Example 2 was carried out except that the blood used was not the patient A but the blood of the patient C. The number of immune cells obtained after 8 days of culture was $8.5 \times 10^7$ and the final lymphocytes isolated from 30 mL of the patient C was $3.53 \times 10^9$ cells.

Experimental Example 1

Figure 1:
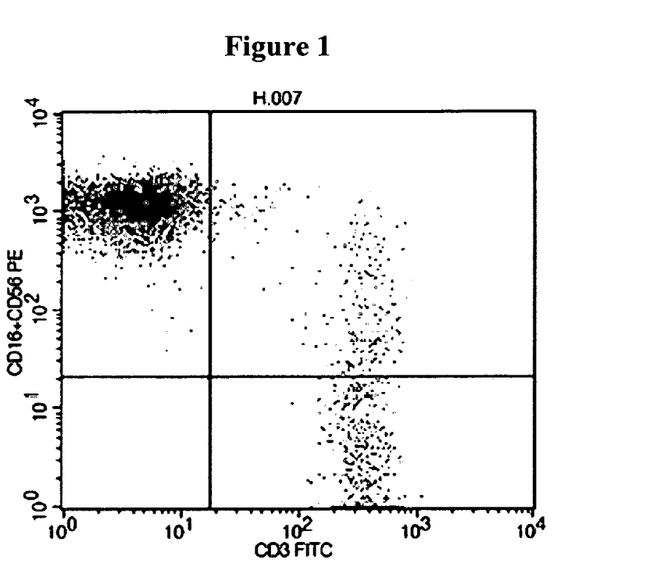
FIG. 1 is a graph showing a phenotype change of activated lymphocytes obtained through the NK cell culture method using the NK cell culture medium addition kit according to an embodiment of the present invention.
Figure 2:
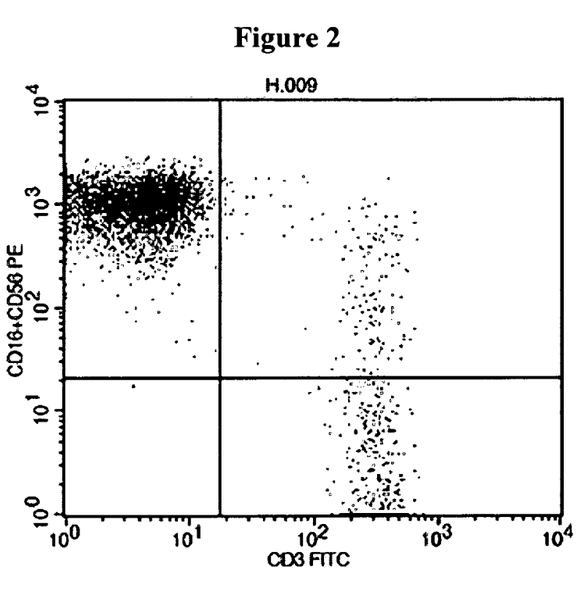
FIG. 2 is a graph showing a phenotype change of activated lymphocytes obtained through the NK cell culture method using the NK cell culture medium addition kit according to another embodiment of the present invention.
Figure 3:
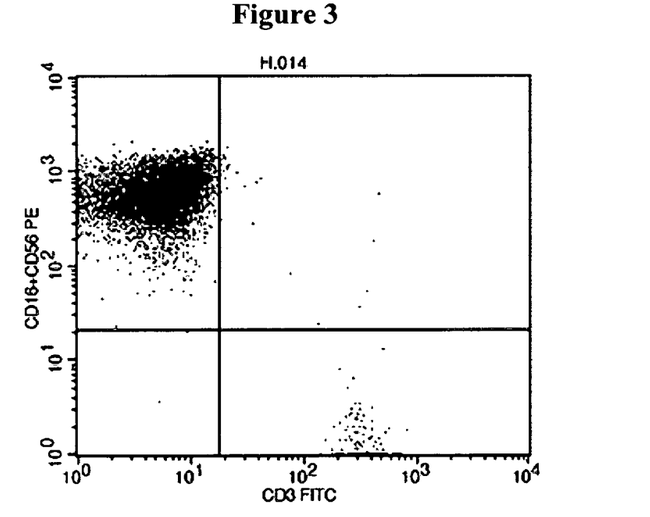
FIG. 3 is a graph showing a phenotype change of activated lymphocytes obtained through the NK cell culture method using the NK cell culture medium addition kit according to the other embodiment of the present invention.

FIGS. 1 to 3 show the analyze result of surface antigens of lymphocytes cultured in the same manner as in Examples 2 to 4 using flowcytometry. FIGS. 1 to 3 are graphs showing the phenotype change of lymphocytes before and after the culture obtained in examples 2 to 4. H1 Region represents the distribution of NK cells, H4 Region represents the distribution of T cell, H2 Region represents the distribution of NKT cells and H3 region represents the distribution of other immune cells.

As shown in FIG. 1, the number of cells proliferated by the culture method of the present invention using the blood of patient A was $3.14 \times 10^9$, the ratio of NK cells was 81.67%, the ratio of NKT cells was 5.82%, the ratio of gdT cells was 5.8%, indicating that about 94% or more of the proliferated cells are active killer cells capable of exhibiting the therapeutic effect.

As shown in FIG. 2, the number of cells proliferated by the culture method of the present invention using the blood of patient B was $4.33 \times 10^9$, the ratio of NK cells was 86.85%, the ratio of NKT cells was 3.45%, the ratio of gdT cells was 0.82%, indicating that about 92% or more of the proliferated cells are active killer cells capable of exhibiting the therapeutic effect.

As shown in FIG. 3, the number of cells proliferated by the culture method of the present invention using the blood of patient C was $3.53 \times 10^9$, the NK cell ratio was 97.81%, the NKT cell ratio was 0.37%, the ratio of gdT cell ratio was 0.06%, indicating that about 98% or more of the proliferated cells are active killer cells capable of exhibiting the therapeutic effect.

As shown in FIGS. 1 to 3, even when the genetic characteristics of the patient changes during the lymphocyte culture, more than almost 80% of the proliferated cells were NK cells, NKT cells and gdT cells, indicating that more than 92% of active killer cells can be homogeneously cultured.

Figure 4A:
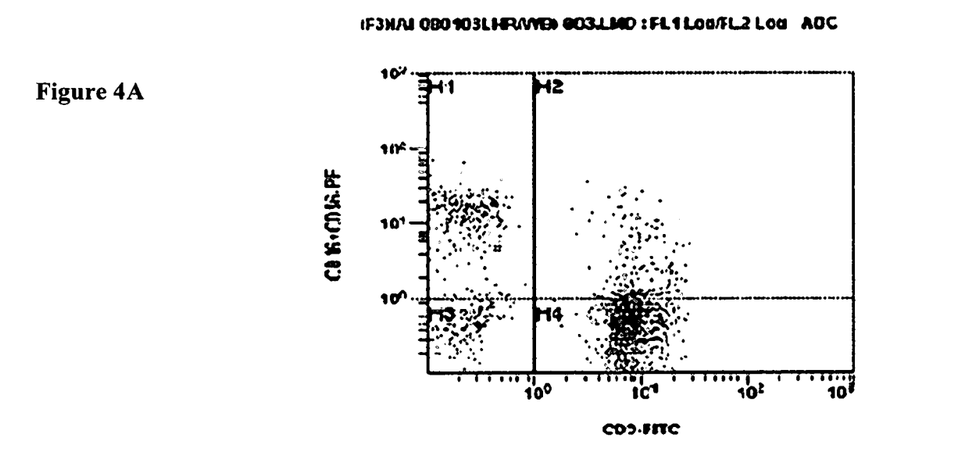
FIG. 4A is a graph showing a phenotype of lymphocytes before using the conventional culture method and FIG. 4B is a graph showing a phenotype change of activated lymphocytes obtained through the conventional culture method in the art.
Figure 4B:
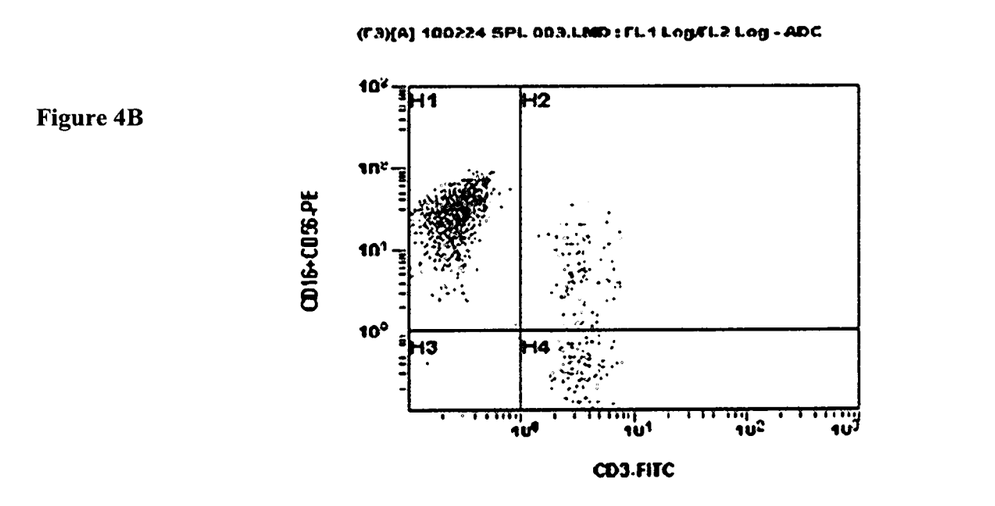

On the other hand, according to the prior art (Patent No. 10-1039843) as shown in FIG. 4, the surface antigen was most distributed in the H4 region before the culture as shown in the graph (a) while after the culture it was mostly distributed in the H1 region as shown in the graph (b). However, it can be clearly seen that the number of proliferated cells was smaller compared to the same in FIGS. 1 to 3.

Experimental Example 2

Lymphocytes cultured in the same manner as in Examples 2 to 4 were used as effector cells and blood cancer cell lines (K562) were used as target cells. The ratio of activated lymphocytes to cancer cells was 10:1, and a potency assay was performed to measure the killing ability of activated lymphocytes against blood cancer cell lines.

The method for testing the activity of K562 cell line is evaluating the extent of killing cancer cells by reacting two cells at 10:1 ratio of effector cell to target cell for 4 hours. However, the titer of lymphocytes cultured in the present invention was too high, killing almost all cancer cells, and therefore, only reacted for two hours in order to increase the discrimination and shorten the time of analysis. The results are shown in the following Table 1.

TABLE 1

| Classification | Example 2 | Example 3 | Example 4 |
|---|---|---|---|
| Potency (%) | 68.2% | 65.9% | 71.4% |

As shown in Table 1, comparing the average potency of the lymphocyte cultured by the conventional culture method is 40-50%, the potency of the lymphocyte cultured by the method of the present invention exhibited 65% or more even when the reaction time was 2 hours, which is 50% shorter than the normal reaction time, indicating the cancer cell killing ability of the lymphocyte cultured by the method of the present invention is extremely excellent.

The high potency of the lymphocytes cultured according to the method of the present invention even when the reaction time is short is due to the high ratio of NK cells in lymphocytes. These results indicate the method of the present invention provides lymphocytes with high ratio of NK cells with prominent cancer cell killing ability and the therapeutic effect.

While the present invention has been particularly shown and described with reference to exemplary embodiments thereof, it is clearly understood that the same is by way of illustration and example only and is not to be taken by way of illustration, various changes and modifications will be possible.

The invention claimed is:

1. A method of culturing natural killer (NK) cells included in lymphocytes separated from blood, the method comprising:
    a) adding an antibody 1 solution to the lymphocytes in a cell culture medium, followed by adding plasma, wherein the antibody 1 solution comprises an anti-CD16 antibody and an anti-CD56 antibody which are dissolved in a basal medium, wherein the anti-CD16 antibody and the anti-CD56 antibody are each present in a concentration of about 0.1 to 15 µg/mL;
    b) adding an antibody-cytokine mixed solution to the culture medium after the step (a), wherein the antibody-cytokine mixed solution comprises a cytokine 1 solution and an anti-CD3 antibody, wherein 1 to 12 µg/mL of the anti-CD3 antibody is dissolved in the cytokine 1 solution, and the anti-CD3 antibody is not immobilized, and wherein the cytokine 1 solution comprises 0.5-5 ng/mL of IL-12 and 2-50 ng/mL IL-18 dissolved in the basal medium;
    c) adding the cytokine 1 solution to the culture medium after the step b), followed by adding plasma;
    d) adding an antibody 2 solution to the cell culture medium after the step c), followed by adding at least one of plasma and FBS, wherein the antibody 2 solution comprises the antibody 1 solution and the basal medium in a volume ratio of 1:6-10;
    e) adding a cytokine 2 solution to the cell culture medium after the step d), followed by adding at least one of plasma and FBS, wherein the cytokine 2 solution comprises 10-50 ng/mL of IL-15 is dissolved in the basal medium;
    f) adding an antibody 3 solution comprising the antibody-2 solution and at least one of plasma and FBS to the cell culture medium after the step e); and
    g) adding the basal medium and at least one of plasma and FBS to the cell culture medium after the step f) to obtain cultured NK cells,
    wherein the basal medium comprises 100-300 ng/mL of IL-2 and 5 mM of L-glutamine dissolved in the cell culture medium, and
    wherein an interval between the step a) and the step (b) is at least 24 hours; and a total duration of culturing the NK cells is 7 to 8 days.

2. The method of claim 1, wherein the plasma is autologous plasma, that is prepared from autologous blood, wherein 40 USP units or more of heparin is added to each ml of the autologous blood.

3. The method of claim 1, wherein the content of the plasma or FBS is less than 10% by volume of the total volume of the cell culture medium.

4. The method of claim 1, wherein the blood is peripheral blood.

* * * * *